United States Patent [19]

Thomas

[11] 4,273,992

[45] Jun. 16, 1981

[54] ELECTRIC HEATING APPARATUS FOR HEAT-TREATING PHARMACEUTICALS

[76] Inventor: Arend J. Thomas, 1361 Chestnut Ave., Annapolis, Md. 21403

[21] Appl. No.: 103,105

[22] Filed: Dec. 13, 1979

[51] Int. Cl.[3] ........................ H05B 1/00; A61M 5/00; F24C 7/04

[52] U.S. Cl. ........................................ 219/521; 34/88; 128/214 A; 219/220; 219/354; 219/405; 219/411; 219/415; 219/418; 362/92

[58] Field of Search ............... 219/521, 354, 347, 348, 219/220, 405, 411, 214, 218, 415, 418, 419, 217; 362/92, 154; 128/214 A; 34/4, 88

[56] References Cited

U.S. PATENT DOCUMENTS

| | | | |
|---|---|---|---|
| 1,444,561 | 2/1923 | Schraeder | 219/347 |
| 1,630,237 | 5/1927 | Smith | 219/417 |
| 1,912,818 | 6/1933 | Becket | 219/521 |
| 1,945,196 | 1/1934 | Kelley | 219/347 X |
| 2,042,855 | 6/1936 | Merklein | 219/347 X |
| 2,057,421 | 10/1936 | Dickson | 219/354 X |
| 2,511,643 | 6/1950 | Lawrence | 219/521 X |

FOREIGN PATENT DOCUMENTS

| | | | |
|---|---|---|---|
| 394980 | 7/1933 | United Kingdom | 219/411 |

OTHER PUBLICATIONS

"The Use of a Microwave Oven To Redissolve Crystallized Mannitol Injection (25%) in Ampuls", Michael L. Kleinberg, et al., Hospital Pharmacy, vol. 14, Jul. 1979, pp. 391, 392.

"Microwave Oven Explosion", Hospital Pharmacy, vol. 14, Oct. 1979, p. 612.

"Warming Kettle For Storing Mannitol Injection", Scott, et al., American Journal of Hospital Pharmacy, vol. 37, No. 1, Jan. 1980, pp. 16, 19 and 24.

*Primary Examiner*—A. Bartis

*Attorney, Agent, or Firm*—Quaintance, Murphy & Richardson

[57] ABSTRACT

An electric heating apparatus for preventing recrystallization or to dissolve existing crystals of pharmaceutical compositions, such as mannitol, which tend to recrystallize during storage. Single dose sealed vials of the pharmaceutical are received in a receptacle having an open top, closed bottom and reflective inner surfaces. A light bulb is supported in the receptacle above the vials and the radiant energy therefrom reflected from the inner surfaces of the receptacle heats the vials.

The light bulb and support therefor are of such dimension that visual observation of the vials through the open top is not obstructed. The support for the light bulb includes a swivel joint permitting horizontal movement of the light bulb to provide access to the interior of the receptacle for removal of the vials. The temperature within the receptacle is controlled by a control means, such as a thermostat, in circuit with the light bulb.

3 Claims, 3 Drawing Figures

ELECTRIC HEATING APPARATUS FOR HEAT-TREATING PHARMACEUTICALS

BACKGROUND OF THE INVENTION

1. Field of the Invention

This invention relates to apparatus for heat-treating pharmaceuticals. More particularly, this invention relates to apparatus for heat-treating mannitol in order to prevent recrystalization of dissolved solid material in a mannitol solution.

2. Statement of Problem and Prior Art Solutions

Mannitol is a widely used diuretic that is injected intraveneously during operations in order to cause patients being operated upon to promptly urinate during the operation so that injurious substances can be passed from the body or so that a urinalysis can be performed while the patient is still on the operating table.

Mannitol tends to recrystalize when stored for any length of time and cannot be injected if crystals are present. In accordance with the usual approach, these crystals are dissolved by either heating the mannitol in a hot water bath or an autoclave while still in the vial or ampule. In accordance with the directions for dissolving crystals in "MANNITOL, MSD" manufactured by the Merick, Sharp & Dohme Company and sold in ampules, crystals are removed by heating a water bath to 80° C., removing the water bath from its heat source and then immersing the ampule of mannitol for fifteen to twenty minutes. In an alternative approach, the ampules of mannitol are autoclaved for twenty minutes at 120° C. (fifteen PSI). As soon as the ampules are cool enough to handle, they are shaken gently and allowed to cool to body temperature before use. The mannitol injection sold by "invenex" is packed in a vial and requires heating to 100° C. or autoclaving for twenty minutes at 120° C. in order to dissolve crystals. The vial containing the mannitol must then be shaken several times as the temperature drops and cooled to body temperature before injecting.

As is readily seen, providing dissolved mannitol on an ongoing basis can be a tedious process. Frequently, all of the mannitol available in a hospital pharmacy is crystalized and must be heat-treated before use. During an operation, the mannitol is needed immediately and the delay necessitated by heat-treating can adversely affect an operation. Even if a program is established for heat-treating mannitol on an ongoing basis, it can be both expensive and inconvenient if the directions supplied with mannitol dosages are complied with. Certainly, boiling water and then immersing mannitol vials in the water is a tedious approach while autoclaving the vial is also a tedious and perhaps expensive approach. An empty autoclave may not be available and in order to ensure that there is always an autoclave available for mannitol, an additional autoclave is sometimes provided at considerable expense. In any event, providing a ready supply of crystal free mannitol is, to say the least, an irritating administrative problem.

The existence of this problem has been long recognized and attempts to redissolve mannitol crystals by using microwave ovens have been suggested. However, there has been one instance of a mannitol vial exploding while in a microwave oven causing considerable damage to the oven and endangering personnel nearby. It has also been suggested to keep mannitol in warming cabinets so that a ready supply of mannitol is available for immediate use. However, warming cabinets are expensive and are not necessarily appropriate dissolving existing crystals. Moreover, warming cabinets are not designed to take the abuse which often occurs in a busy hospital pharmacy in which vials may from time-to-time be broken and spilled within the cabinets. Accordingly, warming cabinets are not widely used to prevent recrystalization of mannitol.

Clearly, there is a need for an alternative cost effective approach which will encourage hospital pharmacies to always have a ready supply of dissolved mannitol available.

SUMMARY OF THE INVENTION

In view of the foregoing considerations, it is a feature of the instant invention to provide an inexpensive, convenient apparatus for heat-treating mannitol so that a ready supply of dissolved mannitol is conveniently available.

The instant invention contemplates a receptacle with a reflective inner surface in which vials or ampules of mannitol are contained and a radiant heat source positioned above the vials or ampules and within the receptacle to heat the vials or ampules and thus keep mannitol within them in a dissolved state.

The instant invention further contemplates a support attached to the receptacle for holding the light bulb over the vials or ampules. The support allows the light bulb to be moved so that the vials may be reached without burning one's hand. Moreover, the instant invention contemplates utilizing either a thermostat or rheostat for controlling current to the light bulb so that the temperature within the recéptable can be maintained at a desired level.

DESCRIPTION OF THE PREFERRED EMBODIMENT

Figure 1:
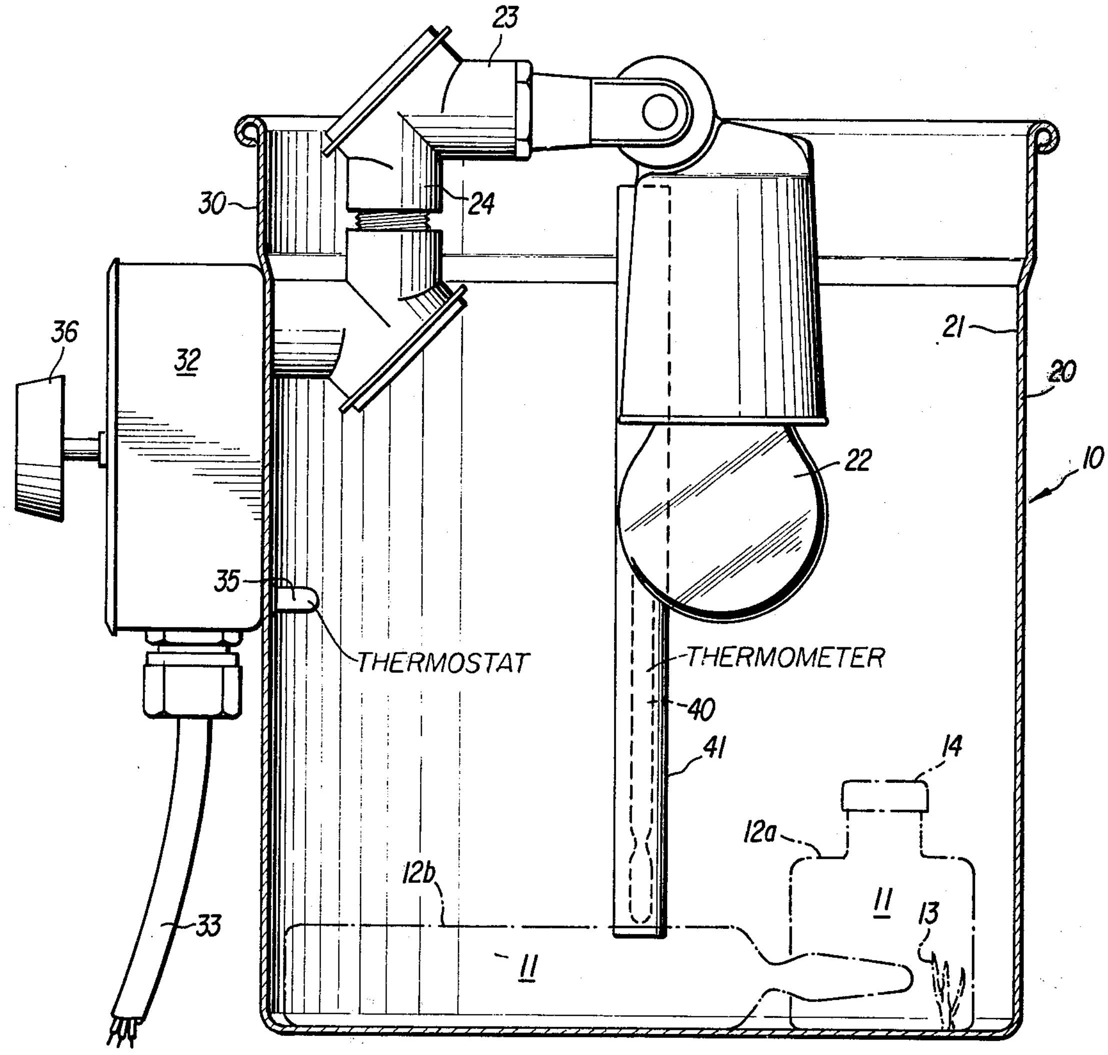
FIG. 1 is a side view of the apparatus in accordance with the instant invention, showing a receptacle for containing vials of mannitol, wherein the receptacle is partly cut away to show just how a light bulb used for heating the mannitol within the vial is mounted.
Figure 2:
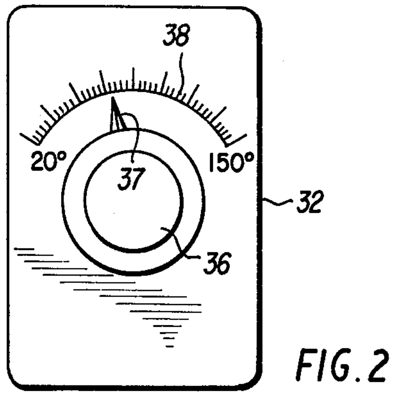
FIG. 2 is a front view of a thermostat dial used to control the temperature within the receptacle.

Referring now to FIG. 1 there is shown an apparatus, designated generally by the numeral 10 for heating and maintaining the temperature level of dissolved mannitol 11 stored within vials 12A and ampules 12B (only one of each is shown). The purpose of the apparatus 10 is to keep the mannitol in the solution 11 from crystalizing into crystals 13 or to redissolve any crystals which have formed. The vial 12B has a metallic cap 14. Vials such as the vials 12B cannot be heated in a microwave oven due to the metal cap.

Figure 3:
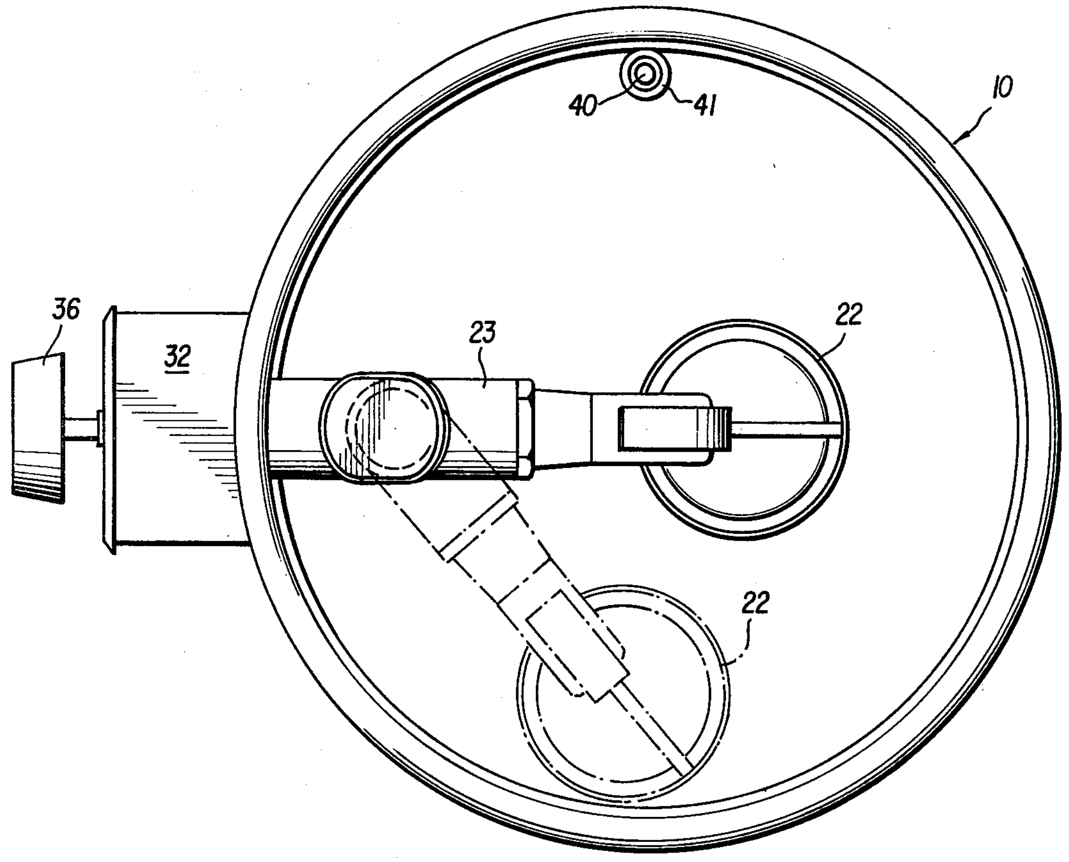
FIG. 3 is a top view showing how the light bulb is mounted to move from a centered position to a side position in order that vials or ampules may be placed in or removed from the receptacle without interfering with the light bulb.

The apparatus includes a receptacle 20 which is preferable a metallic receptacle with a highly reflective interior surface 21. A light bulb 22 is suspended within the receptacle 20 by a universal type fixture or bracket 23. As is seen in FIG. 3, the light bulb 22 can swivel from the solid line position to the dotted line position so that the vials 12 can be conveniently placed in and removed from the receptacle 20. This is accomplished by a conventional swivel joint 24 in the fixture 23. The joint 24 has stops thereon to limit the arc through which the bulb swivels so that the bulb cannot be slammed against the inner surface 21 of the receptacle 20 and shatter.

Positioned on the outer surface 30 of the receptacle 20 is a control box 32 which is used to control power flowing to the light bulb 22 via a power cord 33. In accordance with a preferred embodiment, the control 32 includes a temperature sensor 35 which projects within the receptacle 20 in order to monitor the temperature. A dial 36 mounted on the control 32 is used to set the desired temperature by aligning a pointer 37 with a scale 38. Preferable, the scale 38 reads from 20° C. to 150° C. When heat treating mannitol the preferable range for the setting is between 35° C. and 50° C. with the preferred point being approximately 40° C. If it is necessary to heat mannitol to dissolve crystals then the temperature within the receptacle may be increased to 100° C. or perhaps 120° C.

In the alternative the control 32 may simply be a rheostat which is adjusted in accordance with readings on a thermometer 40. The thermometer 40 may be a dial type of thermometer or perhaps a mercury type of thermometer held within the interior of the receptacle 20 by a tube 41. For the sake of convenience, the dial 36 is also a switch which can be pressed to either energize the bulb 22 or to deenergize the bulb 22.

In practice, the receptacle 20 utilized is a metallic container made of stainless steel, 9 inches in inner diameter and 10 inches high. The light bulb 22 utilized is a 75 watt bulb. It was found that by maintaining mannitol at 40° C., cooling to room temperature occurred on removing the ampules or vials from the receptacles and allowing them to stand for 15 minutes. The mannitol can be injected upon cooling to either body temperature or room temperature. It has been found that redissolved mannitol can be kept in the receptacle 20 for at least 6 months without recrystalization occurring when the receptacle is kept at a temperature of 40° C. It is not known how long the redissolved mannitol can be stored, but it is surmised that the storage in the redissolved state will exceed the recommended life of the mannitol.

The advantages of the aforedescribed apparatus 10 are numerous. In addition to providing a ready supply of dissolved mannitol, the mannitol can be conveniently removed from the container by hand without burning one's hand, the outside of the receptacle 20 remains cool enough so as to not be hazardous, and the apparatus is relatively inexpensive to manufacture since it is made of readily available components.

The foregoing embodiment is merely illustrative of the invention which is to be limited only by the following claims.

What is claimed is:

1. An apparatus for heat-treating pharmaceuticals, such as mannitol solutions contained in sealed enclosures, the apparatus comprising:

a receptacle for receiving the sealed enclosure, said receptacle having a reflective inner surface, an open top and a closed bottom;

a light bulb for providing radiant energy to the interior of said receptacle whereby the energy reflects from the reflective inner surface and onto the sealed enclosures to heat the pharmaceutical therein;

means mounted on the receptacle for supporting the light bulb within the receptacle, beneath the top of the receptacle and in substantial spaced relation to the bottom of the receptacle, wherein the light bulb is above the sealed enclosures, said light bulb and the support being of a dimension less than that of the open top of the receptacle wherein visual observation to the bottom of the receptacle is unobstructed and the presence of sealed enclosures in the receptacle can be determined by looking through the open top of the receptacle, said supporting means including a joint allowing horizontal movement of the light bulb to provide convenient access to the interior of said receptacle for removal of the sealed enclosures; and means for controlling the temperature within the receptacle by controlling energy supplied to the light bulb.

2. The apparatus of claim 1 wherein the receptacle is a cylindrical metal container.

3. The apparatus of claim 1 wherein the receptacle is a cylindrical metal container approximately 9 inches in diameter and 10 inches high.

* * * * *